United States Patent [19]

Wilt, Jr.

[11] Patent Number: 4,511,157
[45] Date of Patent: Apr. 16, 1985

[54] APPARATUS FOR FACILITATING INTRAVENOUS FEEDING DURING TRANSPORTATION OF PATIENT

[75] Inventor: Chester F. Wilt, Jr., Scottsdale, Ariz.

[73] Assignee: St. Joseph's Hospital and Medical Center, Phoenix, Ariz.

[21] Appl. No.: 399,823

[22] Filed: Jul. 19, 1982

[51] Int. Cl.³ .............................................. A47C 7/62
[52] U.S. Cl. ........................... 280/289 WC; 248/125; 297/188; 297/DIG. 4
[58] Field of Search ....... 280/289 WC, 289 R, 289 A, 280/292, 242 WC; 248/125; 297/188, 192, 217, DIG. 4; 180/DIG. 3

[56] References Cited

U.S. PATENT DOCUMENTS

| | | | |
|---|---|---|---|
| 2,596,055 | 5/1952 | Thomas | 280/289 WC |
| 3,709,556 | 1/1973 | Allard et al. | 248/125 X |
| 4,332,378 | 6/1982 | Pryor | 248/125 X |

Primary Examiner—Joseph F. Peters, Jr.
Assistant Examiner—Mitchell J. Hill
Attorney, Agent, or Firm—Drummond & Nissle

[57] ABSTRACT

Apparatus for interconnecting a wheelchair and portable wheeled IV stand to maintain the wheelchair and IV stand in fixed spaced relationship with respect to one another when the wheelchair is being pushed by a medical attendant.

3 Claims, 5 Drawing Figures

U.S. Patent    Apr. 16, 1985    4,511,157
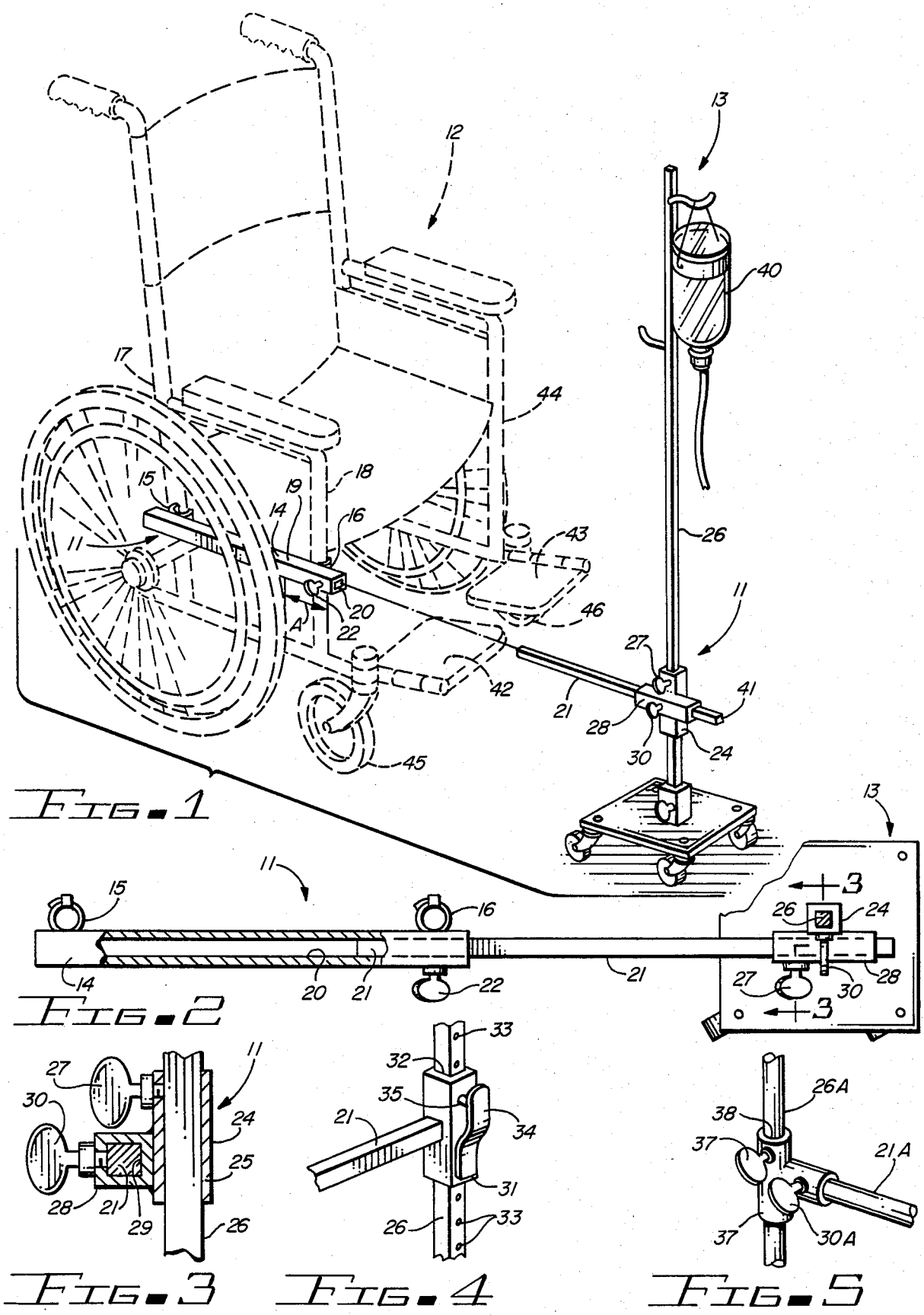

APPARATUS FOR FACILITATING INTRAVENOUS FEEDING DURING TRANSPORTATION OF PATIENT

This invention pertains to apparatus for facilitating intravenous feeding during transportation of a patient.

More particularly, the invention relates to apparatus which interconnects a wheelchair and portable, wheeled IV stand and maintains the IV stand at a fixed distance from the wheelchair when the wheelchair is being pushed along the ground.

In a further respect, the invention pertains to apparatus for interconnecting an IV stand and a wheelchair, the apparatus being adapted to be secured to a wheelchair and to be detachably connected to a portable, wheeled IV stand so that the IV stand can be quickly detached from the apparatus when a patient is transferred from the wheelchair to a gurney or to a hospital bed.

Intravenous, or "IV", feeding equipment typically includes an upstanding pole provided with a hook for carrying fluid containers. Each upstanding pole is either directly attached to a bed, wheelchair or gurney or is mounted on a supporting base having wheels which permit the upstanding pole and base to be pushed along the ground. There are disadvantages associated with the use of either IV poles directly attached to beds or other hospital equipment or with the use of portable IV poles carried by wheeled dollies. If IV poles are directly affixed to wheelchairs and gurneys, when a patient is transferred from a gurney to a wheelchair the IV container must also be transferred from the IV pole on the gurney to the IV pole on the wheelchair. Since IV poles are commonly adapted to carry equipment in addition to a fluid container, for instance a mini-computer for monitoring the rate of flow of fluid from the fluid container through the transfer tube to the patient, transferring all the equipment from the gurney IV pole to the wheelchair IV pole, or vice versa, is time consuming and, if any of the equipment is inadvertently dropped, can cause a patient marked discomfort.

When a portable IV stand is utilized, an additional attendant is normally required to push and to control the IV stand while another attendant pushes the patient in a wheelchair or gurney. If one attendant attempts to control both a wheelchair (or gurney) and a portable IV stand, or if the patient grasps the IV pole while being wheeled along, there is an increased probability that the IV stand may tip over or may accidentally travel too far away from the patient, causing an excessive amount of pressure to be placed on the needles in the patient's body. In particular, if the IV stand tips over, the patient is likely to undergo a painful and traumatic experience.

Accordingly, it would be highly desirable to provide improved apparatus for intravenously administering fluids to a patient while the patient is in transit and is being transferred between wheelchairs, gurneys or other hospital equipment.

It would also be highly desirable to provide improved apparatus for intravenous feeding of a patient which would readily incorporate and utilize existing wheelchairs, gurneys and portable IV stands and which would enable a single medical attendant to conveniently simultaneously control a wheelchair (or gurney) and an IV stand.

It would further be desirable to provide improved apparatus for intravenous feeding of patients which would eliminate or minimize the necessity of transferring fluid containers from one IV stand to another when a patient is moved between wheelchairs, gurneys and other hospital equipment.

Therefore, it is a principal object of the invention to provide improved apparatus which facilitates intravenous administration of fluids to a patient being moved about and transferred between wheelchairs, gurneys and other hospital equipment.

A further object of the invention is to provide improved apparatus for intravenously administering fluids wherein the apparatus incorporates and utilizes existing wheelchairs, gurneys and portable IV stands.

Another object of the invention is to provide improved intravenous fluid administration apparatus which enables a single medical attendant to simultaneously move and readily control a wheelchair (or gurney) and a portable, wheeled IV stand.

Still a further object of the instant invention is to provide improved intravenous fluid administration apparatus which eliminates or minimizes the necessity of transferring fluid containers and other equipment from one IV stand to another when a patient is moved from a wheelchair to a gurney or vice versa.

These and other, further and more specific objects and advantages of the invention will be apparent to those skilled in the art from the following detailed description thereof, taken in conjunction with the drawings, in which:

FIG. 1 is a perspective view of one of the presently preferred embodiments of the invention in combination with a wheelchair and a portable IV stand;

FIG. 2 is an enlarged top view of the apparatus of FIG. 1 illustrating further construction details thereof;

FIG. 3 is a section view of a portion of the apparatus of FIG. 2 taken along section line 3—3 thereof;

FIG. 4 is a perspective view of a portion of the apparatus of FIG. 1 adapted in accordance with another embodiment of the invention; and FIG. 5 is a perspective view of a portion of the apparatus of FIG. 1 adapted in accordance with still a further embodiment of the invention.

Briefly, in accordance with my invention, I provide substantially rigid means for interconnecting and maintaining an IV stand and a wheelchair in generally fixed spaced relationship with respect to one another when the wheelchair and IV stand are wheeled along the ground. The IV stand includes a base, an upstanding elongate pole mounted on said base and adapted to carry a fluid container, and ground engaging wheels rotatably mounted on the base. The wheelchair includes a frame, a seat mounted on the frame, and ground engaging wheels rotatably mounted on the frame. The substantially rigid means for interconnecting the IV stand and wheelchair is attached at one end to the wheelchair, is attached at another end to the IV stand and spans the distance separating the wheelchair and IV stand. When an individual pushes the wheelchair, the interconnecting means maintains the IV stand in fixed spaced relationship with respect to the wheelchair and allows the IV stand to move in the same direction and at the same rate of travel as the wheelchair.

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates one embodiment of the invention, generally indicated by reference character 11, interconnecting wheelchair 12 and portable IV stand 13. Stand 13 carries fluid container 40. Apparatus 11 includes elongate rectangular member 14 having clips 15, 16 which are respectively positioned and tightened around vertically disposed frame members 17, 18 of wheelchair 12. Member 14 could be welded or otherwise attached to the frame of wheelchair 12. It is presently preferred that member 14 be detachably affixed to the frame of wheelchair 12 so that member 14 can, when desired, be readily taken off wheelchair 12 and installed on another wheelchair. Although member 14 is, in FIG. 1, connected to a pair of frame members of wheelchair 12, member 14 could be cut along dashed lines 19 such that only the length of member 14 indicated by arrow A was attached to a single frame member 16. The remaining portion of member 14, including clasp 15, would simply be discarded. A short length of member 14, indicated by reference character A, could be attached to only a single frame member of wheelchair 12 as long as the means for attaching member 14 to the frame member was sufficiently strong to withstand torque and other forces generated on member 14 during the combined travel of wheelchair 12 and IV stand 13.

Elongate rectangular aperture 20 of member 14 slidably receives elongate rectangular rod 21. When rod 21 is inserted in aperture 20, set screw 22, carried by member 14, is turned against rod 21 to hold rod 21 in position in aperture 20. Elongate rectangular aperture 25, passing through sleeve 24, is sized so sleeve 24 slides along rectangular pole 26 of portable IV stand 13. When sleeve 24 is moved to the desired position along pole 26, set screw 27 carried by sleeve 24 is turned to force the end of set screw 27 into and against pole 26 to maintain sleeve 24 in position on pole 26. Elongate rectangular aperture 29 formed through horizontally disposed sleeve 28, carried by sleeve 24, is shaped and dimensioned to slidably receive rod 21. When rod 21 has been passed through aperture 29 of sleeve 28 the desired amount, set screw 30 rotatably carried by sleeve 28 is turned into and against rod 21 to fixedly maintain rod 21 in position in sleeve 28.

As shown in FIG. 4, in another embodiment of the invention, rod 21 could carry vertically disposed rectangular sleeve 31 having elongate aperture 32 formed therethrough to slidably receive upstanding pole 26 of portable IV stand 13. Apertures 33 are formed in pole 26 at spaced points along the length thereof. Sleeve 31 carries spring steel thumb 34 which presses pin 35 on thumb 34 inwardly toward pole 26 and into one of apertures 33. In order to adjust the position of sleeve 31 on pole 26, pin 35 is retracted from one of apertures 33 and sleeve 31 is slid to another position where pin 35 snaps into another aperture 33.

Although a rectangular IV pole 26 is desirable since it basically eliminates the problem of the IV pole rotating in sleeve 24, many existing portable IV stands include vertical upstanding poles which are cylindrically shaped. As depicted in FIG. 5, a cylindrical upstanding IV pole 26A could be provided with sleeve 37 having elongate cylindrical aperture 38 formed therethrough and sized to slidably receive cylindrical pole 26A. When sleeve 37 is moved to the desired height on pole 26A, set screw 39 carried by sleeve 37 is turned against pole 26A to maintain sleeve 37 in position on pole 26A.

In use, support member 14 is detachably fixedly connected to the frame of a wheelchair and sleeve units 24, 28 are attached to portable IV stands 13. When a patient is in bed or on a gurney and is being intravenously administered fluids the IV fluid container 40 is carried by a portable IV stand 13. After the patient is transferred from the bed to a wheelchair 12, sleeve 24 is adjusted to the proper height along rod 26 and extension rod 21 is slidably inserted through elongate rectangular aperture 29 of sleeve 28. When rod 21 has been pushed through aperture 29 of sleeve 28 the desired distance, thumb screw 30 is tightened to maintain rod 21 in fixed position with respect to sleeve 28. If a patient has a broken hip or broken bone in the upper leg and is wearing a body cast which causes his right leg, when the patient is seated in wheelchair 12, to project outwardly generally horizontal to the ground, thumb screw 30 can be tightened near the far end 41 of rod 21 so that portable IV stand 13 is positioned in front of the patient's right foot and tends to run interference for and protect the patient's foot. If each of the patient's legs can, when the patient is seated in wheelchair 12, be bent at the knee so that the patient's feet are on support boards 42, 43 of wheelchair 12 then a substantial portion of the length of rod 21 can be inserted into aperture 20 of member 14 so that IV stand 13 is positioned immediately adjacent wheelchair 12. Once a medical attendant has pushed wheelchair 12 and the patient carried therein to a particular destination, for instance, to an examination table or to another bed, thumb screw 30 is loosened and IV stand 13 is pulled away from wheelchair 12 so member 21 slides free of sleeve 28. Thumb screw 22 on member 14 can be loosened and rod 21 pushed completely into aperture 20 for storage. The patient is then transferred to the examination table or bed and the IV stand positioned nearby. The wheelchair may be retained for later use or taken to another location to transfer another patient.

In some instances, sleeves 24, 31 or 37 shown in FIGS. 1-5 cannot be readily installed on pole 26 of an existing portable IV stand because a hook or other object secured to the pole prevents the sleeves from being slid onto one end and to the center portion of pole 26. In these cases the sleeve assembly can be attached to end 41 of extendable arm 21 and adapted to detachably fixedly engage pole 26 without having to be slid over one end of pole 26. A variety of clamping or jaw mechanisms which would close around pole 26 and could be opened to release pole 26 could be incorporated into the sleeve assembly to accomplish this purpose. While the capability of readily attaching and detaching a portable IV stand 13 to and from apparatus 11 increases the flexibility of the apparatus, in some cases it might be desirable to weld or otherwise permanently attach an IV stand 13 to apparatus 11.

Elongate member 14 could, if desired, be horizontally disposed and attached to vertical wheelchair frame members 18, 44 generally perpendicular to the position of member 14 shown in FIG. 1. Attaching member 14 to frame members 18, 44 would permit IV stand 13 to be positioned off to the side of wheelchair 12 instead of being positioned in front of the wheelchair as shown in FIG. 1. Depending on the desired position of IV stand 13 with respect to wheelchair 12, member 14 could be attached in any orientation to any other frame member or members of wheelchair 12.

Apparatus 11, when attached to and interconnecting a wheelchair 12 and portable IV stand as shown in FIG. 1, maintains the wheelchair and IV stand in generally constant spaced relationship with respect to one another such that the distance from the wheelchair to the IV stand remains fixed, the position or placement of the IV stand with respect to the wheelchair remains fixed, and the wheelchair and IV stand move along simultaneously at the same rate of speed when the wheelchair is being pushed by a medical attendant.

In contrast to the IV pole shown in U.S. Pat. No. 3,709,556 to Allard, et al., the apparatus of the invention, when used in conjunction with portable IV stands, generally eliminates the necessity of transferring fluid container 40 from one IV stand to another when a patient is transferred from a bed to a wheelchair or vice versa. Apparatus 11 also eliminates the necessity of utilizing a second medical attendant to push portable IV stand 13 or of having the patient in the wheelchair attempt to control IV stand 13 when a first medical attendant is pushing wheelchair 12.

Although in some applications it might be desirable to utilize elastic or resilient material to produce members 14, 21 and sleeves 24, 28, in the presently preferred embodiments of the invention apparatus 21 is substantially rigid so that when a medical attendant tips wheelchair 12 back so front wheels 45, 46 are raised from the ground to move the wheelchair over a bump, the wheels of IV stand 13 are also raised from the ground.

Having described my invention in such terms as to enable those skilled in the art to understand and practice it, and having identified the presently preferred embodiments thereof, I claim:

1. In combination with a portable IV stand and a wheelchair, said IV stand including
    a base,
    an upstanding elongate pole mounted on said base and adapted to carry an IV bottle, and
    ground engaging wheels rotatably mounted on said base,
said wheelchair including
    a frame,
    a seat mounted on said frame,
    primary ground engaging wheels rotatably mounted rearwardly on said frame,
    secondary ground engaging wheels rotatably mounted forwardly on said frame, said secondary wheels being smaller than said primary wheels, said frame being shaped, contoured and dimensioned such that an individual standing behind said wheelchair can backwardly tilt said wheelchair on said primary wheels to raise said secondary wheels and the forward part of said frame upwardly away from the ground,
substantially rigid means for interconnecting and maintaining said IV stand and said wheelchair in generally fixed spaced relationship with respect to one another when said wheelchair and IV stand are wheeled along the ground, said interconnecting means
    (a) being attached at one end to said wheelchair;
    (b) being attached at another end to said IV stand;
    (c) spanning the distance separating said wheelchair and said IV stand; and,
    (d) maintaining said IV stand in front of said wheelchair;
such that when an individual behind said wheelchair
    (e) pushes said wheechair said IV stand moves in the same direction of and at the same rate of travel as said wheelchair and is generally maintained in said fixed, spaced relationship with respect to said wheelchair; and,
    (f) backwardly tilts said wheelchair to raise said secondary wheels of said wheelchair off of the ground said ground engaging wheels of said portable IV stand are raised from the ground to facilitate passage of said IV stand and said wheelchair over an obstruction on the ground.

2. The apparatus of claim 1 wherein said interconnecting means is adapted such that said IV stand is readily disconnected from said interconnecting means and separated from said wheelchair.

3. The apparatus of claim 2 wherein said interconnecting means includes an elongate member spanning the distance between said wheelchair and said portable IV stand.

* * * * *